US011160444B1

(12) United States Patent
D'Aquanni et al.

(10) Patent No.: US 11,160,444 B1
(45) Date of Patent: Nov. 2, 2021

(54) SLOTTED IMAGING PROBE

(71) Applicant: Nanosurgery Technology Corporation, Sarasota, FL (US)

(72) Inventors: Peter J. D'Aquanni, Murrieta, CA (US); Sam Seiichiro Ochi, Lakewood Ranch, FL (US); Mark Walter, Sarasota, FL (US)

(73) Assignee: Nanosurgery Technology Corporation, Sarasota, FL (US)

( * ) Notice: Subject to any disclaimer, the term of this patent is extended or adjusted under 35 U.S.C. 154(b) by 456 days.

(21) Appl. No.: 16/016,464

(22) Filed: Jun. 22, 2018

Related U.S. Application Data

(60) Provisional application No. 62/524,364, filed on Jun. 23, 2017.

(51) Int. Cl.
| | |
|---|---|
| *A61B 1/05* | (2006.01) |
| *A61B 1/07* | (2006.01) |
| *A61B 1/317* | (2006.01) |
| *A61B 1/00* | (2006.01) |
| *A61B 17/34* | (2006.01) |

(52) U.S. Cl.
CPC ............ *A61B 1/051* (2013.01); *A61B 1/0011* (2013.01); *A61B 1/00096* (2013.01); *A61B 1/00154* (2013.01); *A61B 1/07* (2013.01); *A61B 1/317* (2013.01); *A61B 17/3415* (2013.01)

(58) Field of Classification Search
CPC ... A61B 1/051; A61B 1/00096; A61B 1/0011; A61B 1/00154; A61B 1/0607; A61B 1/07; A61B 1/317; A61B 17/3421; A61B 17/3415
See application file for complete search history.

(56) References Cited

U.S. PATENT DOCUMENTS

| | | | | |
|---|---|---|---|---|
| 4,904,048 A * | 2/1990 | Sogawa | ............... | A61B 1/0058 385/118 |
| 5,621,830 A * | 4/1997 | Lucey | ................ | A61B 1/00179 385/118 |
| 5,647,840 A * | 7/1997 | D'Amelio | .......... | A61B 1/00091 600/169 |
| 10,120,102 B2 * | 11/2018 | Tsakalakos | ............ | G01V 9/005 |
| 2013/0172673 A1 * | 7/2013 | Kennedy, II | ......... | A61B 1/0125 600/109 |
| 2017/0290492 A1 * | 10/2017 | Hamm | ............... | A61B 1/00135 |
| 2018/0084986 A1 * | 3/2018 | Ochi | ...................... | A61B 1/015 |
| 2019/0004254 A1 * | 1/2019 | Yoshino | ............... | G02B 6/3897 |
| 2020/0046213 A1 * | 2/2020 | Bendory | ............. | A61B 1/0669 |

* cited by examiner

*Primary Examiner* — Timothy J Neal
*Assistant Examiner* — William B Chou

(57) ABSTRACT

An apparatus includes a slotted tube having a plurality of first slots and a plurality of second slots; an imager disposed in the slotted tube, the imager having a plurality of corners arranged in the plurality of first slots; and a plurality of light guides disposed in the plurality of second slots.

19 Claims, 9 Drawing Sheets

SLOTTED IMAGING PROBE

CROSS-REFERENCE TO RELATED APPLICATIONS

This application claims the benefit of U.S. Provisional Patent Application No. 62/524,364, filed on Jun. 23, 2017, which is incorporated by reference herein for all purposes. A U.S. Nonprovisional patent application Ser. No. 16/016,471 entitled "TRIMMED IMAGER PROBE," filed with the U.S. Patent and Trademark Office on the same day as the present application on Jun. 22, 2018, and assigned to the same applicant as the present application, is also incorporated by reference herein for all purposes.

BACKGROUND

Surgical interventions provide significant mechanisms for diagnosing and treating disease, injuries, pain, and other medical problems. Surgical procedures, however, can cause problems of their own. For example, open surgical procedures often include forming large incisions, which can become infected, can cause pain, and/or can take a long time to heal. The various complications associated with open surgery can significantly impact a patient's quality of life, and can even cause permanent medical problems or even death. These complications can also increase the costs associated with medical care.

Minimally, or non-, invasive, procedures can be used to diagnose and treat the same medical problems as open procedures, without the same risk of complications. A surgeon performing a minimally invasive procedure on a patient can see and treat a therapeutic target by inserting a camera and a surgical tool into the patient's body, and visualizing and/or treating the therapeutic target remotely. Even when the tool is inserted through an incision, the incision is relatively small. As a result, large incisions—and the risks associated with large incisions—can be avoided.

Arthroscopy is a minimally invasive surgical procedure for diagnosing and treating problems inside of a patient's joint. Using arthroscopy, a surgeon can see an injury in a patient's knee by forming a small incision in the patient's skin, and inserting a device known as an "arthroscope" through the incision. The arthroscope includes a camera, which enables the surgeon to see whether any tissues (e.g., cartilage, ligaments, bone, etc.) within the knee are damaged. The damaged tissue can then be treated, repaired, or both.

Because a substantial portion of minimally invasive procedures require operators to remotely view subdermal structures, many minimally invasive devices include imaging devices. In particular, semiconductor imaging devices can be used in a variety of minimally invasive surgical devices, such as arthroscopes, to produce digital images or video that can be displayed to an operator during a minimally invasive procedure.

However, the applicability of existing imaging devices in minimally invasive devices are limited by their sizes. For example, many high-quality imaging devices are too large to be incorporated into minimally invasive surgical devices.

SUMMARY

According to various embodiments, an apparatus includes a slotted tube having a plurality of first slots and a plurality of second slots; an imager disposed in the slotted tube, the imager having a plurality of corners arranged in the plurality of first slots; and a plurality of light guides disposed in the plurality of second slots.

In some embodiments, the plurality of first slots and the plurality of second slots are rectangular trenches in the slotted tube that extend from a distal end of the slotted tube.

In some embodiments, the plurality of second slots are longer and wider than the plurality of first slots.

In some embodiments, the imager has a polygonal cross-section, the plurality of corners being corners of the polygonal cross-section.

In some embodiments, the plurality of corners of the imager are parallel to an axis of the slotted tube.

In some embodiments, a number of the plurality of corners of the imager is equal to a number of the plurality of light guides, and the plurality of first slots are circumferentially located in the slotted tube between the plurality of second slots.

In some embodiments, the imager includes a plurality of image sensors and a plurality of light tubes extending from the plurality of image sensors, respectively.

In some embodiments, each of the plurality of light guides is a fiber optic cable.

In some embodiments, the apparatus further includes a lens disposed on a distal end of the slotted tube and configured to focus light on the imager.

In some embodiments, the apparatus further includes a plurality of contacts disposed on a proximal end of the imager.

In some embodiments, the plurality of contacts are configured to supply a voltage to the imager and to receive image data from the imager.

In some embodiments, the apparatus further includes an interposer disposed inside of the slotted tube and proximal to the imager, the interposer being connected to the plurality of contacts.

In various embodiments, a method includes generating a slotted tube by forming a plurality of first slots and a plurality of second slots in a tube; placing an imager in the slotted tube, a plurality of corners of the imager being arranged in the plurality of first slots; and threading the plurality of light guides through the plurality of second slots.

In some embodiments, generating the slotted tube by forming the plurality of first slots and the plurality of second slots in the tube includes sawing a metal tube.

In some embodiments, generating the slotted tube by forming the plurality of first slots and the plurality of second slots in the tube includes laser cutting a metal tube.

In some embodiments, the method further includes gluing the imager and the plurality of light guides to the slotted tube.

In various embodiments, an apparatus includes a needle; and a probe disposed in the needle, the probe including: a slotted tube having a plurality of first slots and a plurality of second slots; an imager disposed in the slotted tube, the imager having a plurality of corners arranged in the plurality of first slots; and a plurality of light guides disposed in the plurality of second slots.

In some embodiments, the apparatus further includes a bulb attached to a proximal end of the needle and a proximal end of the probe; and a hub disposed on the bulb, the hub being configured to extend and retract a distal end of the probe from a distal end of the needle.

DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

DETAILED DESCRIPTION

Figure 1A:
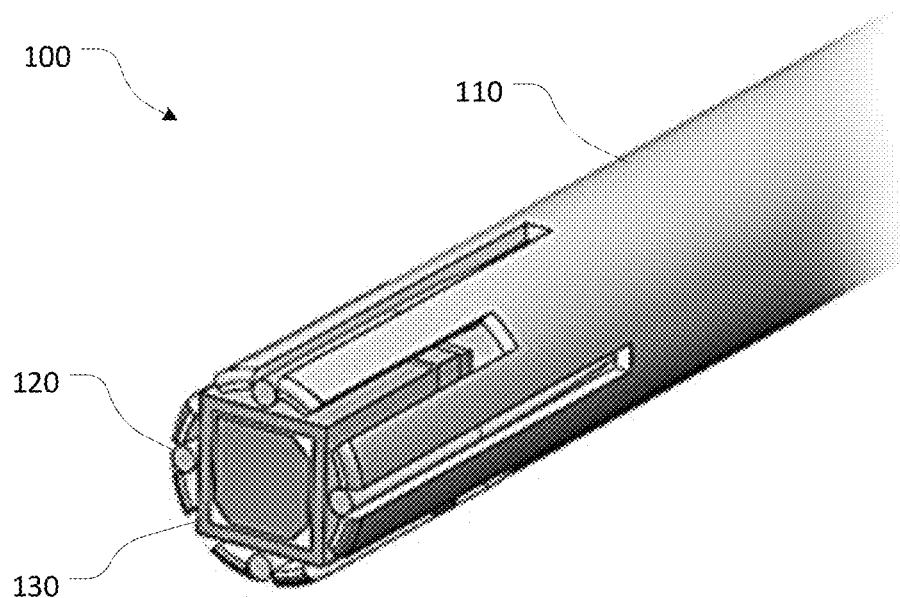
FIGS. 1A and 1B illustrate an imaging probe according to an embodiment of the present disclosure.

Throughout the present disclosure, reference is made to particular features of various embodiments of the invention. Embodiments of the invention encompass all possible combination of the disclosed features. For example, where a particular feature is disclosed in the context of a particular aspect, implementation, or embodiment, or is disclosed in a particular claim, that feature can also be used, to the extent possible, in combination with and/or in the context of any other aspect, implementation, or embodiment.

When a method or process including two or more defined steps is described herein, the defined steps can be carried out in any order or simultaneously, except where the context excludes that possibility. For example, a disclosed method including defined steps can include one or more steps carried out before the defined steps, can include one or more steps carried out after the defined steps, can include one or more steps carried out between the defined steps, or a combination thereof.

The terms "comprises" and "includes," as well as their grammatical equivalents, indicate that other components, ingredients, steps, etc. are optionally present. For example, an article "comprising" components A, B, and C, can consist of only components A, B, and C, or can contain not only components A, B, and C, but also one or more other components.

The terms "cubic" or "cuboid" each indicate a prism having a square cross-section that is perpendicular to the joining edges of the prism. As used herein, a cubic or cuboid shape is not necessarily a right prism having two base faces that are perpendicular to the joining edges. Furthermore, as used herein, the faces of a cubic or cuboid are not necessarily square. For example, the faces of the cubic or cuboid shape can be rectangular.

The terms "proximate" and "distal," as well as their grammatical equivalents, indicate a relative position. As used herein, a "proximate" structure can be considered a "distal" structure, when a "distal" structure is considered a "proximate" structure.

A probe for remotely imaging features inside of a patient's body includes an imager inside of a tube, e.g., a rigid, cylindrical tube. When the probe is inserted into the patient's body, e.g., subdermally, the imager images the features through a distal end of the tube.

The imager, however, is not necessarily the same shape as the tube. For example, the imager may be cubic, such that when the imager is placed inside of the tube and the corners of the imager abut against the inner surface of the tube, four empty spaces are formed between sides of the imager and the inner surface of the tube. In this configuration, the inner surface of the tube has to be at least as wide as a diagonal width of the imager.

According to embodiments of the present disclosure, corners of the imager are arranged within slots in a wall of the tube, which minimizes empty spaces between the imager and the tube. Other structures in the probe, such as light guides, can also be arranged in slots in the tube. Due to the slots in the tube, the width of the probe can be minimized.

Figure 1B:
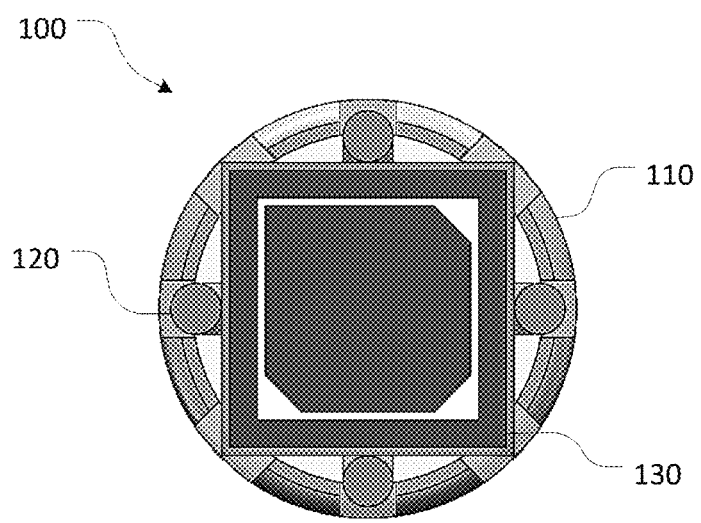

FIGS. 1A and 1B illustrate an imaging probe 100 according to an embodiment of the present disclosure. The imaging probe 100 includes a slotted tube 110, a plurality of light guides 120, and an imager 130.

The slotted tube 110 is a rigid, cylindrical tube that partially encloses the plurality of light guides 120 and the imager 130. A plurality of slots are located in a wall of the slotted tube 110. The light guides 120 are threaded through some of the plurality of slots, and corners of the imager 130 are disposed in the other plurality of slots. Because of the slots, the slotted tube 110 is able to accommodate the imager 130 even though a diagonal width of the imager 130 is longer than the inner width of the slotted tube 110.

The plurality of light guides 120 are configured to emit light that illuminates an area being imaged by the imager 130. The illumination provided by the plurality of light guides 120 can improve the quality of images or video acquired by the imager 130. The light guides 120 are substantially cylindrical and parallel to the slotted tube 110. In some embodiments, the plurality of light guides 120 are fiber-optic cables.

The imager 130 is disposed in the slotted tube 110, and is flanked on multiple sides by the light guides 120. The imager is configured to acquire images from the imaging probe 100.

Although the slotted tube 110 is cylindrical, the imager 130 is not. In various embodiments, the slotted tube 110 has a circular cross-section, but the imager 130 has a polygonal cross-section, such as a square cross-section, as illustrated in FIGS. 1A and 1B. That is, the imager 130 has multiple corners.

As illustrated in FIGS. 1A and 1B, the corners of the imager 130 fit into some of the slots of the slotted tube 110, whereas other portions of the imager fit inside of the inner surface of the slotted tube 110. Other slots in the slotted tube accommodate the light guides 120, which are disposed, threaded, or otherwise present in the slots. In some embodiments, the slots through which the light guides 120 are threaded are wider and longer than the slots through which the corners of the imager 130 are disposed. That is, the slots accommodating the light guides 120 extend farther from a distal end of the slotted tube 110 than the slots accommodating the corners of the imager 130.

Although not illustrated, in some embodiments, the imager 130 and the light guides 120 are attached to the slotted tube 110 with a glue that is disposed inside of the slots. In certain embodiments, the imager 130 is held in place with respect to the slotted tube 110 by a structure that generates a frictional force between the imager and the slotted tube 110, e.g., a device including a spring.

Due to the slots in the slotted tube 110, the imaging probe 100 has a smaller diameter than other probes that accommodate the same imager chip.

Figure 2:
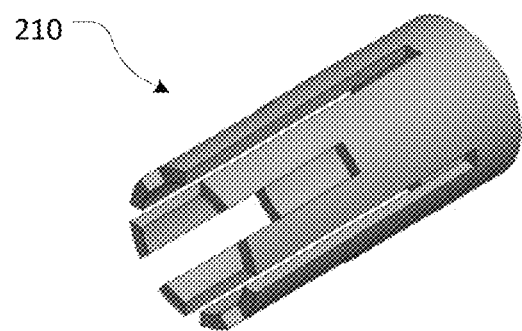
FIG. 2 illustrates a slotted tube according to an embodiment of the present disclosure.

FIG. 2 illustrates a slotted tube 210 according to an embodiment of the present disclosure.

The slotted tube 210 is cylindrically shaped. A plurality of slots extend in the wall of the slotted tube 210 from a distal end of the slotted tube 210. As illustrated, the slotted tube 210 includes four slots that can accommodate four light guides, and four slots that can accommodate four corners of an imager.

In some embodiments, the slotted tube 210 is a metal tube, such as a stainless steel tube. For example, the slotted tube 210 is a blunt, 18 gauge needle.

The slots in the slotted tube 210 have various shapes and lengths depending on the shapes of the light guides and the imager that fit into the slots. For example, the slots are rectangular openings in the wall of the slotted tube 210, as illustrated in FIG. 2.

Figure 3A:
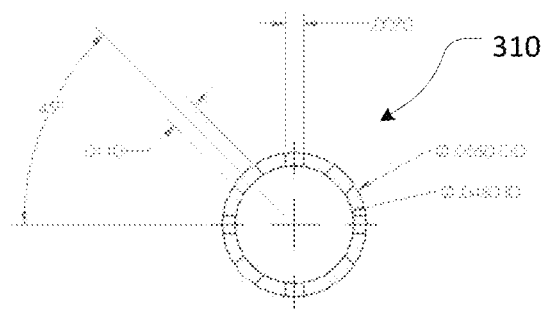
FIGS. 3A and 3B are drawings of a slotted tube according to an embodiment of the present disclosure.
Figure 3B:
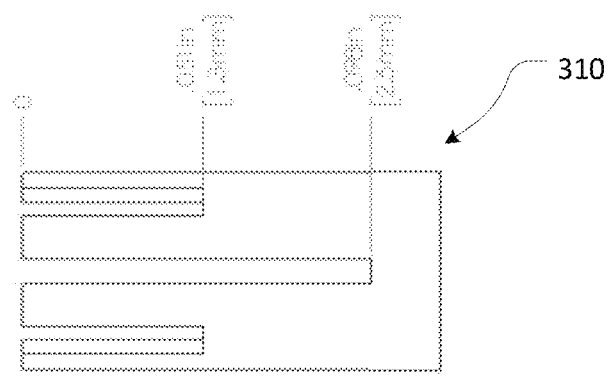

FIGS. 3A and 3B are drawings of a slotted tube 310 according to an embodiment of the present disclosure.

The slotted tube 310 includes first slots that can accommodate light guides, and second slots that can accommodate corners of an imager. The first slots are evenly spaced around the circumference of the slotted tube 310, and the second slots are circumferentially located between the first slots. As illustrated in FIGS. 3A and 3B, the slotted tube 310 includes four first slots and four second slots.

Each of the four first slots are narrower than each of the four second slots. In a specific example, the slotted tube is formed from an 18 gauge needle, each of the first slots has a width of 0.0070 inches and a length of 0.98 inches, each of the second slots has a width of 0.110 inches and a length of 0.51 inches, and each of the first slots is located 45 degrees from a neighboring second slot, and vice versa. However, other dimensions are possible in other embodiments.

Figure 4A:
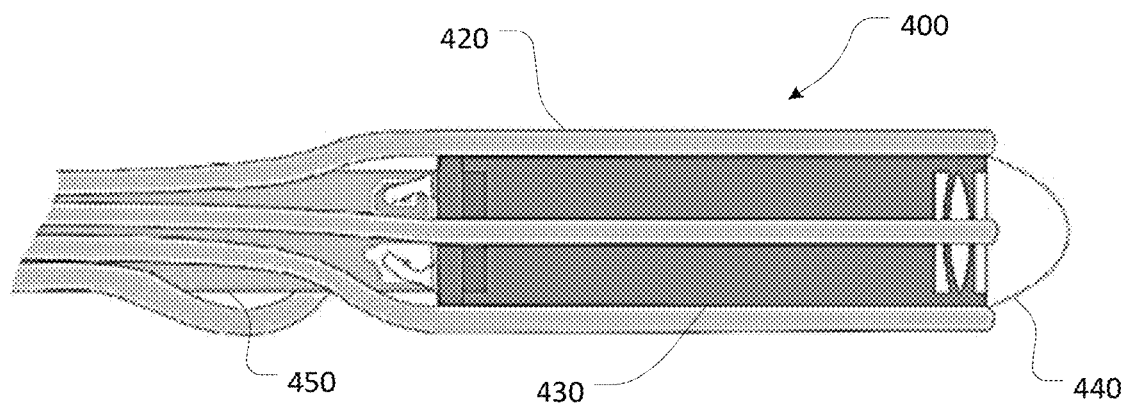
FIGS. 4A and 4B illustrate an imager assembly according to an embodiment of the present disclosure.
Figure 4B:
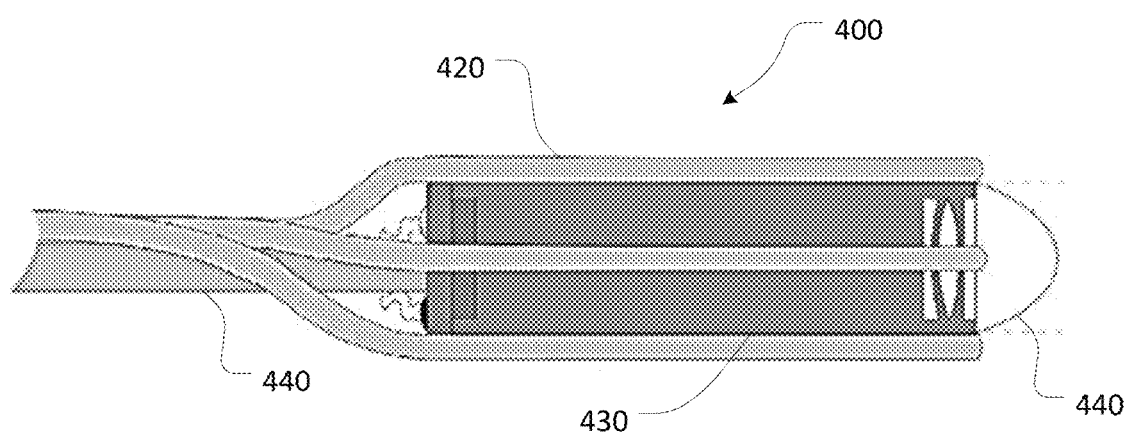

FIGS. 4A and 4B illustrate an imager assembly 400 according to an embodiment of the present disclosure. The imager assembly 400 includes a plurality of light guides 420, an imager 430, a lens 440, and an interposer 450.

The light guides 420 extend along outer surfaces of the imager 430, and are configured to illuminate spaces and structures being imaged by the imager 430. In various embodiments, each light guide 420 is disposed along a different surface of the imager 430.

The imager 430 is configured to capture images, video, or both. The imager 430 includes a plurality of image sensors respectively corresponding to a plurality of pixels. In some embodiments, the imager 450 is cubic, and has a square cross-section.

The lens 440 is configured to focus light on the imager. For example, the lens 440 focuses light on the image sensors in the imager 430. The lens 440 extends from a distal end of the imager 430.

The interposer 450 is disposed proximate to the imager 430, and is configured to electrically connect to the light guides 420 and the imager 430 via a plurality of leads. For example, the interposer 450 supplies power to the imager 430 and the light guides 420. In some embodiments, the interposer 450 supplies control signals to the imager 430, and receives image data from the imager 430 in the form of electrical signals.

In some embodiments, the imager assembly 400 is assembled with a slotted tube, such as any of the slotted tubes 110, 210, and 310 described above. For example, the light guides 420 and corners of the imager 430 are disposed in slots of the slotted tube, the lens 440 extends from a distal end of the slotted tube, and the interposer 450 is disposed inside of the slotted tube.

Figure 5A:
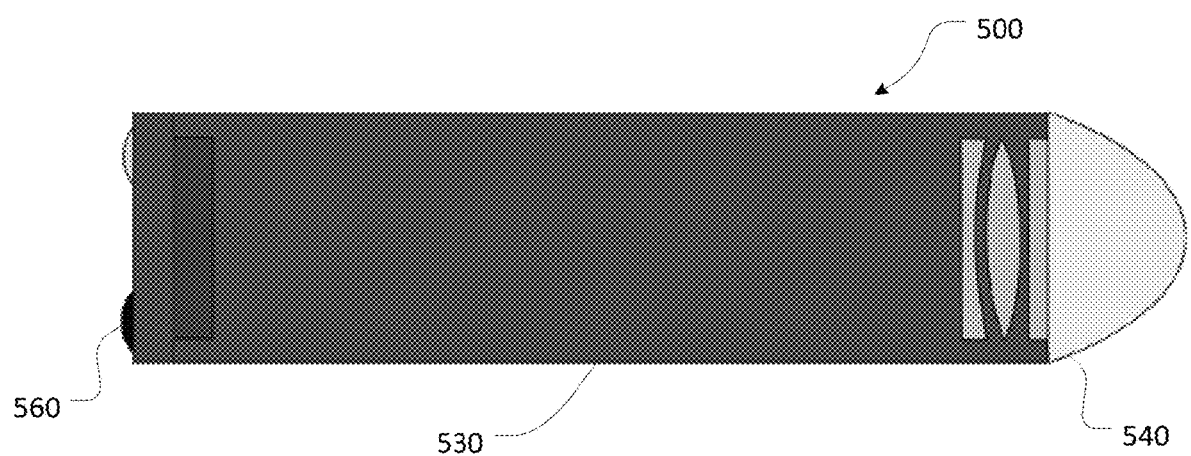
FIGS. 5A to 5C illustrate an imager module according to an embodiment of the present disclosure.
Figure 5B:
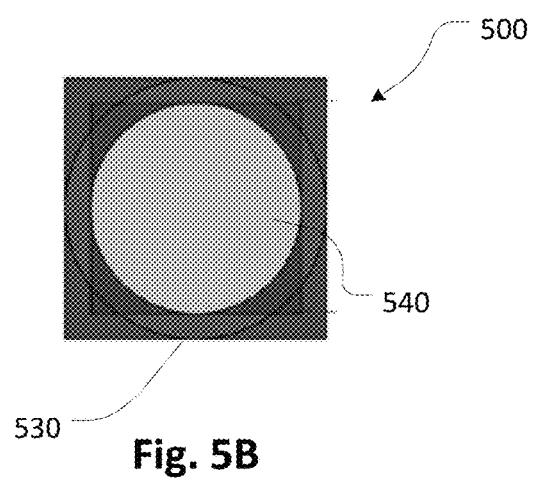
Figure 5C:
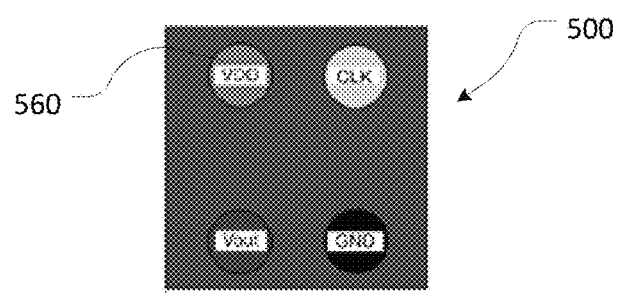

FIGS. 5A to 5C illustrate an imager module 500 according to an embodiment of the present disclosure. The imager module 500 includes an imager 530, a lens 540, and a plurality of contacts 560.

The imager 530 is configured to capture images and/or video through the lens 540, and output image data through the plurality of contacts 560 based on the captured images and/or video. In some embodiments, the imager 530 is a digital image sensor. For example, the imager 530 is a CameraCubeChip manufactured by Omnivision.

The lens 540 is configured to focus light on the imager 530. By focusing the light on the imager 530, the lens 540 improves the quality of the images and/or video captured by the imager 530, for example. In various embodiments, the lens 540 includes a transparent material. The lens 540 is, for example, a Fresnel lens. In some embodiments, the imager 530 and the lens 540 collectively comprise a bee-eye imager.

The plurality of contacts 560 are configured to supply the imager 530 with a voltage that powers the imager 530, to supply a clock signal used by the imager 530, and to receive image data from the imager 530 in the form of electrical signals output by the imager 530.

The plurality of contacts 560 include an input voltage contact VDD, a clock contact CLK, an output voltage contact Vout, and a ground contact GND. The input voltage contact VDD supplies a voltage used to power the imager 530. The clock contact CLK supplies a clock signal to the imager 530. The output voltage contact Vout receives image data from the imager 530 in the form of electrical signals. The image data includes the images and/or video captured by the imager 530 that has been encoded into the electrical signals. The ground contact GND supplies a ground voltage to the imager 530.

Although not illustrated in FIGS. 5A to 5C, the plurality of contacts 560 can be electrically connected to an interposer that has a plurality of corresponding contacts. In some embodiments, the interposer and the imager module 500 are disposed in a slotted tube.

Figure 6:
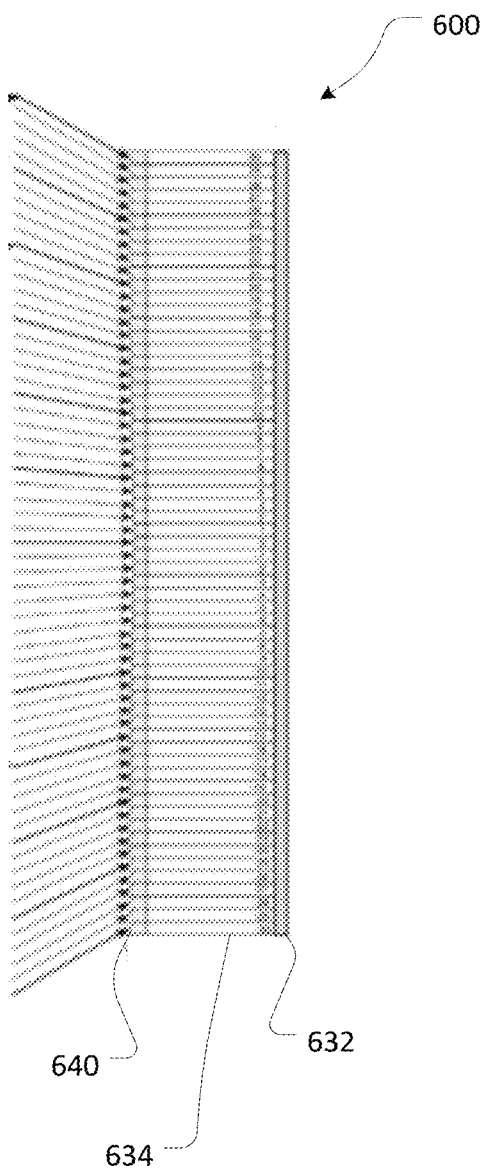
FIG. 6 illustrates a bee-eye imager according to an embodiment of the present disclosure.

FIG. 6 illustrates a bee-eye imager 600 according to an embodiment of the present disclosure. The bee-eye imager 600 includes an image sensor array 632, a plurality of light tubes 634, and a lens 640. In some embodiments, the image sensor array 632 and the plurality of light tubes 634 comprise the imager 530 described above with reference to FIGS. 5A to 5C.

The image sensor array 632 includes a plurality of image sensors arranged in rows and columns. With reference to FIG. 6, the rows extend in a depth direction and the columns extend in a vertical direction. Each one of the plurality of image sensors corresponds to a pixel. In some embodiments, each of the image sensors is a semiconductor device including a plurality of semiconductor layers. For example, each of the image sensors is a complementary metal oxide semiconductor (CMOS) image sensor.

The plurality of light tubes 634 direct light to the plurality of image sensors in the image sensor array 632, respectively, from the lens 640.

The lens 640 focuses light on the image sensor array 632. The lens 640 is a Fresnel lens, for example.

Figure 7:
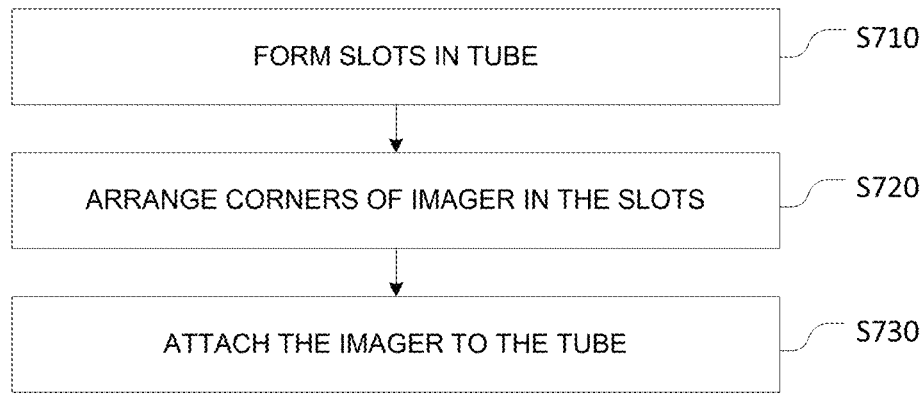
FIG. 7 is a flow-chart describing a method for fabricating an imaging probe according to an embodiment of the present disclosure.

FIG. 7 is a flow-chart describing a method 700 for fabricating an imaging probe according to an embodiment of the present disclosure. The method 700 includes forming slots in a tube at S710, arranging corners of an imager in the slots at S720, and attaching the imager to the tube at S730.

At S710, the slots are cut out of an unslotted tube, e.g., a metal tube. In some embodiments, the slots are generated using a saw blade. In certain embodiments, the slots are laser-cut from the unslotted tube.

The corners of the imager are arranged in the slots at S720 by placing the imager inside of the slotted tube. The slots in the slotted tube correspond to the positions of the corners of the imager. For example, if the imager has a square cross-section with four corners, the slots are evenly spaced circumferentially around the tube.

At S730, the imager is attached to the tube while the corners of the imager are arranged in the slots. For example, the imager is glued to the tube. Suitable glues include epoxy-based adhesives, silicone-based adhesives, ultraviolet (UV)-cured adhesives, epoxy-polyurethane blend adhesives, cyanoacrylate-based adhesives, or a combination thereof.

Figure 8:
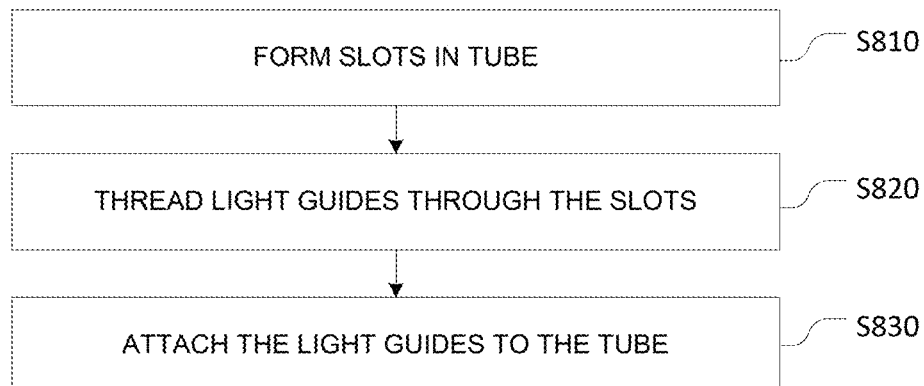
FIG. 8 is a flow-chart describing a method for fabricating an imaging probe according to an embodiment of the present disclosure.

FIG. 8 is a flow-chart describing a method 800 for fabricating an imaging probe according to an embodiment of the present disclosure. The method 800 includes forming slots in a tube at S810, threading the light guides through the slots at S820, and attaching the light guides to the tube at S730.

At S810, the slots are cut out of an unslotted tube, e.g., a metal tube. In some embodiments, the slots are generated using a saw blade. In certain embodiments, the slots are laser-cut from the unslotted tube.

The light guides are threaded through the slots at S820 by arranging the light guides in the slots. The light guides are therefore disposed in the slots.

At S830, the light guides are attached to the tube while the light guides are disposed in the slots. For example, the light guides are glued to the tube. Suitable glues include epoxy-based adhesives, silicone-based adhesives, ultraviolet (UV)-cured adhesives, epoxy-polyurethane blend adhesives, cyanoacrylate-based adhesives, or a combination thereof.

In various embodiments, the methods 700 and 800 are combined to generate the same device that includes an imager and light guides. For example, first slots are generated in method 700 to accommodate the imager, and second slots are generated in method 800 to accommodate the light guides.

Various embodiments of the present disclosure relate to an imaging probe. An imaging probe according to an embodiment of the present disclosure can be used in a variety of minimally invasive surgical devices. Examples of minimally invasive devices are found in, for example, U.S. application Ser. No. 15/261,743, entitled "IMAGING NEEDLE APPARATUS" and published as U.S. Pub. No. 2017/0070654; U.S. application Ser. No. 15/444,180, entitled "VIDEO NEEDLE SYRINGE" and published as U.S. Pub. No. 2017/0245890; U.S. application Ser. No. 15/721,376, entitled "VIDEO NEEDLE SYRINGE" and published as U.S. Pub. No. 2018/0084986; and U.S. application Ser. No. 15/036,609, entitled "IMAGING NEEDLE APPARATUS" and published as U.S. Pub. No. 2017/0100020; all of which are incorporated by reference herein in their entirety.

Figure 9A:
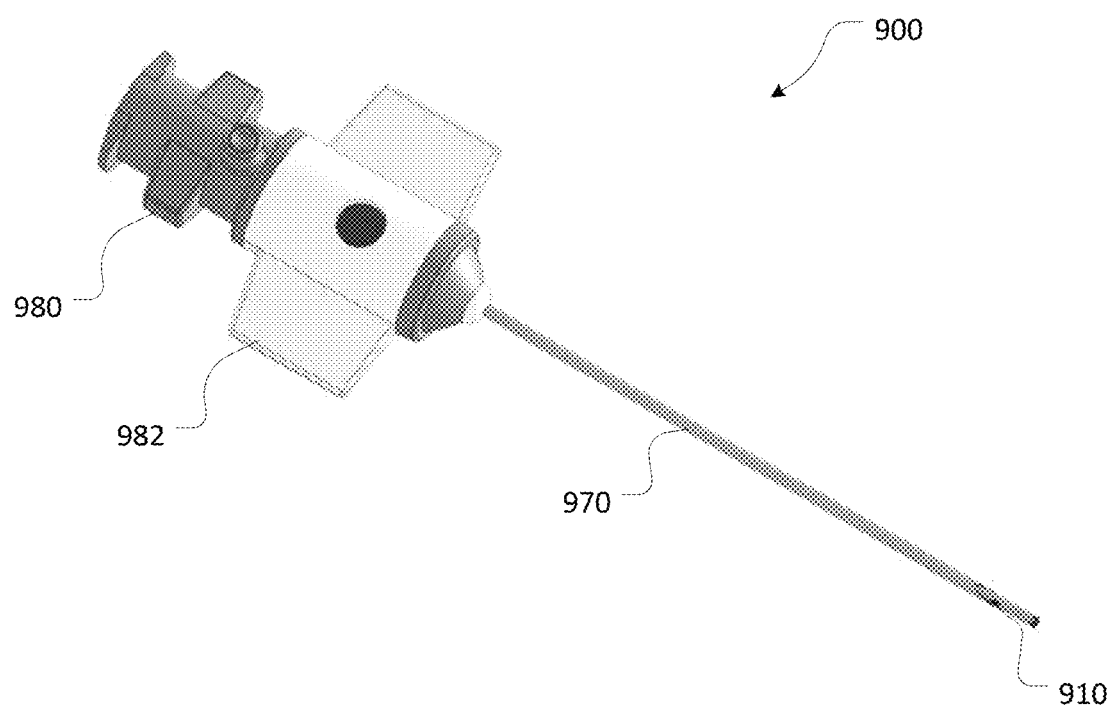
FIGS. 9A and 9B illustrate an imaging needle according to an embodiment of the present disclosure.
Figure 9B:
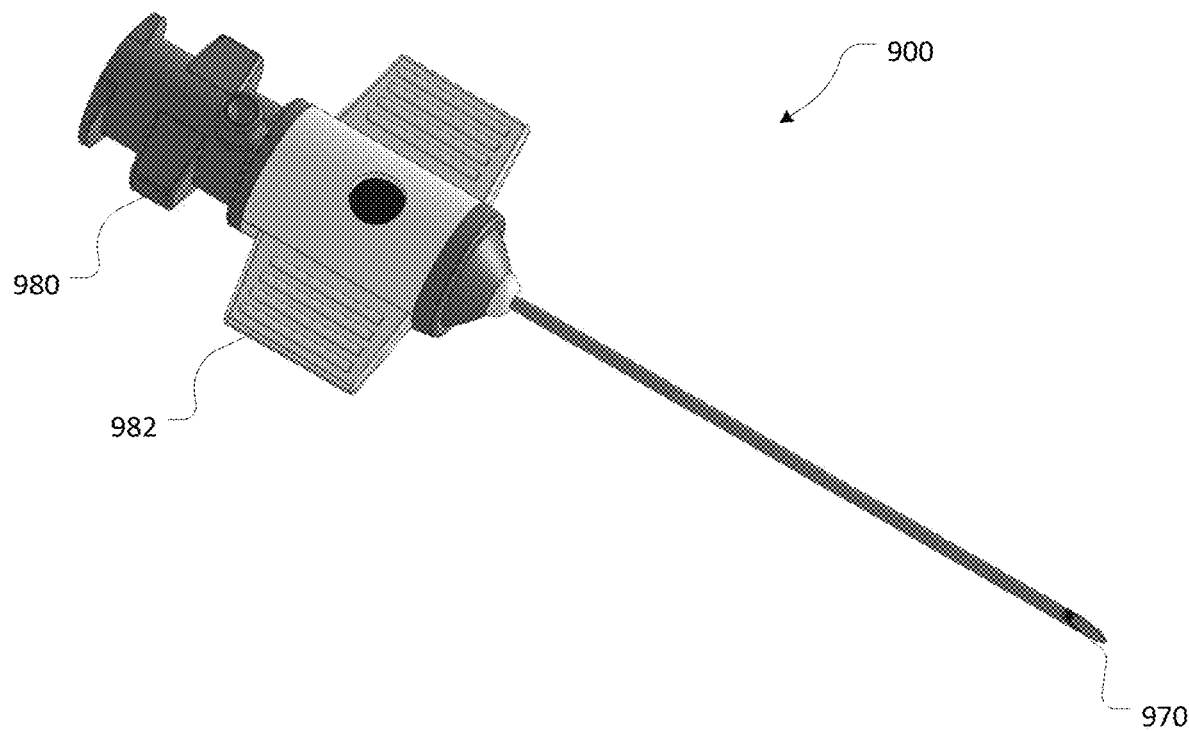

FIGS. 9A and 9B illustrate an imaging needle 900 according to an embodiment of the present disclosure. The imaging needle 900 includes an imaging probe 910, a needle 970, and a bulb 980.

The imaging probe 910 is retractable with respect to the needle 970, and is configured to be inserted underneath the skin of a patient, and image areas of interest. For example, when a user operates a hub 982 on the bulb 980, a distal end of the imaging probe 910 can be extended from the distal end of the needle 970 (as illustrated in FIG. 9A), or retracted from a distal end of the needle 970 (as illustrated in FIG. 9B).

In some embodiments, the imaging probe 910 is the imaging probe 100 described above with reference to FIGS. 1A and 1B. That is, the imaging probe 910 includes an imager and a plurality of light guides disposed in a slotted tube, such that corners of the imagers and the light guides are disposed within slots in the slotted tube. The slots of the tube and the imager are located at a distal end of the imaging probe 910, in various implementations.

The imaging probe 910 can further include one or more holes that are located proximate to the imager. These holes are configured to expel fluid when the imaging probe 910 is in an extended position. In some embodiments, the holes are configured to deliver a therapeutic fluid to an area of interest within a patient. For example, the holes expel a stem cell solution stored inside of the imaging probe 910.

The needle 970 is configured to pierce soft tissue, so that the imaging probe 910 can be inserted into an area of interest underneath a patient's skin. The needle 970 is disposed around the imaging probe 910. A distal end of the needle 970 is sharp, and capable of piercing soft tissue.

The bulb 980 supports the imaging probe 910 and the needle 970, and is configured to be held and operated by a user, e.g., a surgeon. The bulb 980 is further configured to exert pressure on the space inside of the imaging probe 910 where the fluid is stored inside of the imaging probe 910, in order to cause the fluid to be expelled through the holes in the imaging probe 910. The bulb 980 also includes the hub 982, which is operated by the user in order to extend and/or retract the imaging probe 910. The imaging probe 910 and the needle 970 extend from the bulb 980.

Figure 10A:
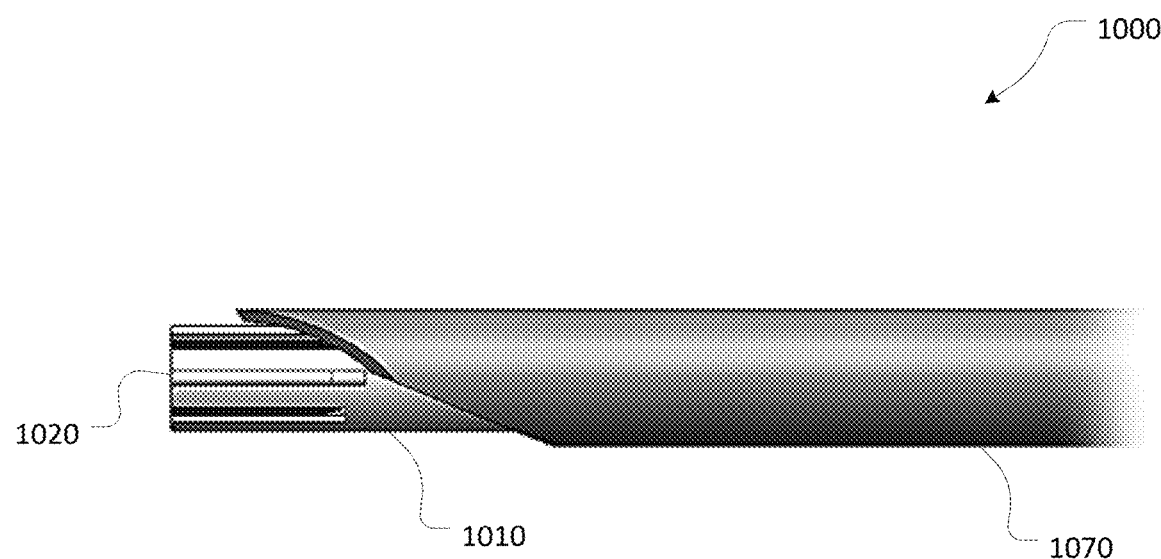
FIGS. 10A and 10B illustrate a distal end of an imaging needle according to an embodiment of the present disclosure.
Figure 10B:
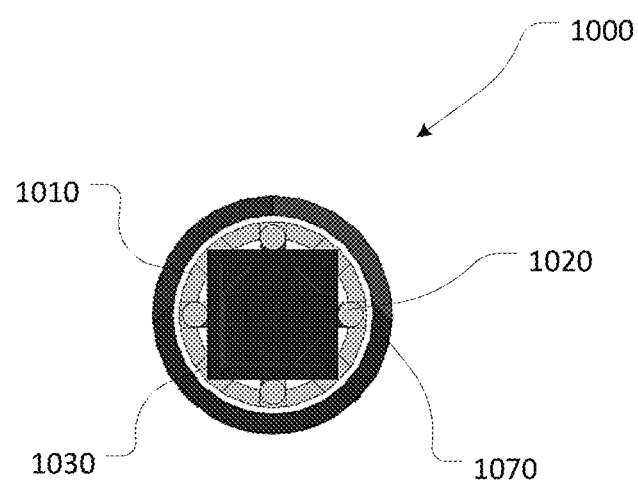

FIGS. 10A and 10B illustrate a distal end 1000 of an imaging needle according to an embodiment of the present disclosure. The distal end 1000 of the imaging needle includes a needle 1070 and a retractable imaging probe extending from the needle 1070.

The imaging probe includes a slotted tube 1010, a plurality of light guides 1020, and an imager 1030. The imager 1030 has a polygonal cross-section. For example, the imager 1030 has a square cross-section. A plurality of corners of the imager 1030 are disposed in first slots in the slotted tube 1010. The light guides 1020 are disposed in second slots in the slotted tube.

The present disclosure relates to an imaging probe with a tube disposed around an integrated imager. The imaging probe can be used to perform a minimally invasive surgical procedure for both diagnosing and treating tissues in a patient's body. For example, the imaging probe can be disposed in a needle as part of a minimally invasive surgical device that can be used as an alternative to an arthroscope.

In an embodiment, the minimally invasive surgical device is significantly smaller than a traditional arthroscope due to the presence of slots in the outer tube, which accommodate corners of the imager. As a result, the device can be used to perform less invasive imaging and treatment procedures in subdermal spaces than traditional arthroscopy.

In an embodiment, the device can be used to both take pictures of a target and to treat the target. For example, the device can be used to take a video of a subdermal tissue, and to deliver a liquid treatment to the tissue. As a result, the apparatus can reduce the cost of minimally invasive treatments.

By integrating diagnostic and therapeutic functions into the same device, embodiments of the present disclosure can reduce the number of incisions for performing a procedure, reduce the damage caused by threading a device through an incision by reducing the number of times equipment is inserted through the incision, and reduce the number of devices required to perform the procedure. As a result, embodiments of the present disclosure can be less invasive and less expensive than traditional surgical tools.

The above specification, examples, and data provide a description of the manufacture and use of the composition of various embodiments of the invention. Since many embodiments of the invention can be made without departing from the spirit and scope of the invention, the invention also resides in the claims hereinafter appended.

What is claimed is:

1. An apparatus, comprising:
   a slotted tube having a wall, the wall having a plurality of first slots and a plurality of second slots, each of the plurality of first slots and each of the plurality of second slots extending from a distal end of the slotted tube;
   an imager disposed in the slotted tube, the imager having a plurality of corners arranged in the plurality of first slots in the wall of the slotted tube; and
   a plurality of light guides each having a portion that is disposed inside a corresponding one of the plurality of second slots in the wall of the slotted tube,
   wherein the plurality of second slots are longer and wider than the plurality of first slots.

2. The apparatus of claim 1, wherein the plurality of first slots and the plurality of second slots are rectangular trenches in the slotted tube.

3. The apparatus of claim 1, wherein the imager has a polygonal cross-section, the plurality of corners being corners of the polygonal cross-section.

4. The apparatus of claim 1, wherein the plurality of corners of the imager are parallel to an axis of the slotted tube.

5. The apparatus of claim 1, wherein a number of the plurality of corners of the imager is equal to a number of the plurality of light guides, and
   wherein the plurality of first slots are circumferentially located in the slotted tube between the plurality of second slots.

6. The apparatus of claim 1, wherein the imager includes a plurality of image sensors and a plurality of light tubes extending from the plurality of image sensors, respectively.

7. The apparatus of claim 1, wherein each of the plurality of light guides is a fiber optic cable.

8. The apparatus of claim 1, further comprising:
   a lens disposed on a distal end of the slotted tube and configured to focus light on the imager.

9. The apparatus of claim 8, further comprising:
   a plurality of contacts disposed on a proximal end of the imager.

10. The apparatus of claim 9, wherein the plurality of contacts are configured to supply a voltage to the imager and to receive image data from the imager.

11. The apparatus of claim 10, further comprising:
    an interposer disposed inside of the slotted tube and proximal to the imager, the interposer being connected to the plurality of contacts.

12. The apparatus of claim 1, wherein a diagonal width of the imager is longer than an inner width of the slotted tube.

13. The apparatus of claim 1, wherein the plurality of corners of the imager fit into the plurality of first slots, respectively.

14. The apparatus of claim 1, wherein the portion of each of the plurality of light guides is a distal portion disposed at the distal end of the slotted tube.

15. A method, comprising:
    providing a slotted tube having a plurality of first slots and a plurality of second slots in a wall of the slotted tube, each of the plurality of first slots and each of the plurality of second slots extending from a distal end of the slotted tube;
    placing an imager in the slotted tube, a plurality of corners of the imager being arranged in the plurality of first slots in the wall of the slotted tube; and
    threading the plurality of light guides through the plurality of second slots in the wall of the slotted tube to expose a portion of each of the plurality of light guides,
    wherein the plurality of second slots are longer and wider than the plurality of first slots.

16. The method of claim 15, wherein generating the slotted tube by forming the plurality of first slots and the plurality of second slots in the tube includes sawing a metal tube.

17. The method of claim 15, wherein generating the slotted tube by forming the plurality of first slots and the plurality of second slots in the tube includes laser cutting a metal tube.

18. An apparatus, comprising:
    a needle; and
    a probe disposed in the needle, the probe including:
    a slotted tube having a wall, the wall having a plurality of first slots and a plurality of second slots, each of the plurality of first slots and each of the plurality of second slots extending from a distal end of the slotted tube;
    an imager disposed in the slotted tube, the imager having a plurality of corners arranged in the plurality of first slots; and
    a plurality of light guides each having a portion disposed inside a corresponding one of the plurality of second slot,
    wherein the plurality of second slots are longer and wider than the plurality of first slots.

19. The apparatus of claim 18, further comprising:
    a bulb attached to a proximal end of the needle and a proximal end of the probe; and
    a hub disposed on the bulb, the hub being configured to extend and retract a distal end of the probe from a distal end of the needle.

* * * * *